(12) United States Patent
Cushman et al.

(10) Patent No.: US 7,781,445 B2
(45) Date of Patent: Aug. 24, 2010

(54) SYNTHESIS OF INDENOISOQUINOLINIUMS AND METHODS OF USE

(75) Inventors: Mark S. Cushman, West Lafayette, IN (US); Alexandra S. Ioanoviciu, San Francisco, CA (US); Yves G. Pommier, Bethesda, MD (US)

(73) Assignees: Purdue Research Foundation, West Lafayette, IN (US); The United States of America as represented by the Department of Health and Human Services, Washington, DC (US)

( * ) Notice: Subject to any disclaimer, the term of this patent is extended or adjusted under 35 U.S.C. 154(b) by 869 days.

(21) Appl. No.: 10/592,849

(22) PCT Filed: Mar. 15, 2005

(86) PCT No.: PCT/US2005/008491

§ 371 (c)(1),
(2), (4) Date: Sep. 14, 2006

(87) PCT Pub. No.: WO2005/089294

PCT Pub. Date: Sep. 29, 2005

(65) Prior Publication Data

US 2008/0242692 A1 Oct. 2, 2008

(51) Int. Cl.
*A61K 31/473* (2006.01)
*C07D 221/18* (2006.01)

(52) U.S. Cl. .................... 514/284; 546/61; 546/48; 546/41; 514/279; 514/280

(58) Field of Classification Search ........... 514/284, 514/280, 279; 546/61, 48, 41
See application file for complete search history.

(56) References Cited

FOREIGN PATENT DOCUMENTS

WO    WO 00/21537    4/2000

OTHER PUBLICATIONS

Compounds with RN 125455-88-1 (published in 1991), RN 7688-89-3 (published in 1968) and RN 264188-39-8 (published in 2002).*

Cushman, Mark et al.; "Synthesis and Antitumor Activity of Structural Analogues of the Anticancer Benzophenanthridine Alkaloid Fagaronine Chloride", J. Med. Chem, 1985, vol. 28, pp. 1031-1036.

Patel, Sanjay S. et al., "Neuromuscular blocking activity of *bis* -4-benzyltetrahydroisoquinolinium esters in the cat". European Journal of Pharmaceutical Sciences, 1995, vol. 4, pp. 63-71.

Wawzonek, S. et al., "The Synthesis and Reactions of 1-Carbamyl-11-ketoindeno[1,2-c]isoquinoline", J. Org. Chem. vol. 31, No. 4, pp. 104-106, 1966.

Strumberg, D. et al., "Synthesis of Cytotoxic Indenoisoquinoline Topoisomerase I Poisons," *J. Med. Chem*, 1999, 42, pp. 446-457.

Jayaraman, M. et al., "Synthesis of New Dihydroindeno[1,2-c]isoquinoline and Indenoisoquinolinium Chloride Topoisomerase I Inhibitors Having High in Vivo Anticancer Activity in the Hollow Fiber Animal Model," *J. Med. Chem.*2002, 45, pp. 242-249.

Kohlhagen et al. "Protein-Linked DNA Strand Breaks Induced by NSC 314622, a Novel Noncamptothecin Topoisomerase I Poison," *Mol. Pharmacol.*1998,54, 50-58).

Cushman et al., "Synthesis of New Indeno[1,2-c]isoquinolines: Cytotoxic Non-Camptothecin Topoisomerase I Inhibitors," *J. Med. Chem.*2000, 43, 3688-3698.

Antony et al., "Differential Induction of Topoisomerase I-DNA Cleavage Complexes by the Indenoisoquinoline MJ-III-65 (NSC 706744) and Camptothecin: Base Sequence Analysis and Activity against Camptothecin-Resistant Topoisomerase I," *Cancer Res.*2003, 63, 7428-7435).

Cushman, M., et al., "Synthesis and Biological Activity of Structural Analogues of the Anticancer Benzophenanthridine Alkaloid Nitidine Chloride," vol. 27, 1984, pp. 544-547.

Dkye, S. F., et al., "The Chemistry of Cryptopine—I, The Epicryptopines," vol. 24, 1968, pp. 1455-1465.

Supplemental European Search Report for European Application no. 05725565.5, dated Oct. 7, 2009, 5 pages.

* cited by examiner

*Primary Examiner*—Charanjit S Aulakh
(74) *Attorney, Agent, or Firm*—Barnes & Thornburg LLP (57) ABSTRACT

Substituted indenoisoquinolinium compounds, and pharmaceutical formulations of substituted indenoisoquinolinium compounds are described. Also described are processes for preparing substituted indenoisoquinolinium compounds. Also described are methods for treating cancer in mammals using the described substituted indenoisoquinolinium compounds or pharmaceutical formulations thereof.

26 Claims, 1 Drawing Sheet

FIG. 1

SYNTHESIS OF INDENOISOQUINOLINIUMS AND METHODS OF USE

GOVERNMENT RIGHTS

The government may have rights in this invention. Funding for this disclosure was provided in part by the National Institutes of Health (NIH) Research Grant UO1 CA89566.

CROSS REFERENCE TO RELATED APPLICATION

This application is a U.S. national counterpart application, filed under 35 U.S.C. §371(c), of international application serial no. PCT/US2005/008491 filed Mar. 15, 2005, which claims the benefit under 35 U.S.C. §119(e) of U.S. provisional patent application Ser. No. 60/553,837 filed Mar. 17, 2004, the disclosures of which are incorporated herein by reference.

TECHNICAL FIELD

The invention described herein pertains to indenoisoquinolinium compounds. The invention described herein also pertains to methods for treating cancer in mammals using indenoisoquinolinium compounds.

BACKGROUND

The control and cure of cancer represents one of our most challenging health problems. The treatment of cancer can be approached by several modes of therapy including surgery, radiation, chemotherapy or a combination of any of these treatments. Chemotherapy continues to be an indispensable therapy for inoperable or metastatic forms of the disease. Thus, the discovery of compounds specifically targeting cancer cells, or the cellular mechanisms involved in the proliferation of cancer cells, can provide significant advancement in the eradication or control of cancer.

The selection of compounds having effective anticancer activity is complicated by the still limited knowledge of cancer cell biology and biochemistry. Therefore, development of new effective anti-cancer agents remains heavily dependent on screening of new compounds for cytotoxic activity. Antineoplastic drug candidates exhibit enhanced cytotoxicity against cancer cells relative to normal cells. Methods of screening for anticancer activity have focused on several targets, (1) the ability of a compound to inhibit tumor growth and/or progression in animal studies; (2) inhibition of cell growth/proliferation in cell lines of cancerous origin; and (3) inhibition of intracellular processes necessary for the growth or propagation of cancer cells.

The mouse L1210 leukemia cell line was initially the preferred model system used for screening compounds for anticancer activity. However, the P388 murine leukemia system was found to be more sensitive and predictive than L1210 leukemia system; it has been used as a primary screen during the past decade. Systematic screening for compounds exhibiting toxicity to these two cell lines has resulted in the isolation of a large number of active natural products. However, the anticancer activities of these compounds were predominantly for leukemia, lymphoma and a few rare tumors. Low clinical efficacy, or the lack of clinical efficacy of known chemotherapeutics against slower growing solid tumors, is a serious concern.

Considering the diversity of cancer in terms of cell type, morphology, growth rate and other cellular characteristics, the U.S. National Cancer Institute (NCI) has developed a disease-oriented approach to anticancer activity screening (M. R. Boyd, in "Principle of Practice of Oncology" J. T. Devita, S. Hellman, S. A. Rosenberg (Eds.) Vol. 3, PPO Update, No. 10, 1989). This in vitro prescreening system is based on the measurement of anticancer cytotoxicity against human cancer cell line panels consisting of approximately 60 cell lines of major human cancers (including leukemia, and slower growing tumor cells such as lung, colon, breast, skin, kidney, etc.) and is referred hereinafter as "COMPARE" screening. An important advantage of the new in vitro screening panels is the opportunity to facilitate identification of compounds that are selectively more cytotoxic to cells of certain types of cancers, thus increasing the ability to select compounds for further study with respect to specific diseases.

Anticancer agents are known to act through a variety of mechanisms to destroy or inhibit the proliferation of cancer cells. For example, some agents are antimetabolites which act as false substrates in the biochemical processes of cancer cells. One compound which has this mechanism of action is methotrexate, an analog of folic acid, which functions in part by binding to dihydrofolate reductase, thereby preventing the formation of guanine and adenine from the folic acid precursor molecule. Thus, methotrexate inhibits the ability of cancer cells to construct DNA by inhibiting the proper metabolism of folic acid.

Other anticancer agents act by alkylating DNA strands, thereby producing defects in the normal double helical structure of the DNA molecule. This alkylation may cause the formation of breaks and inappropriate links between (or within) strands of DNA. Such disruption of the DNA structure, if not repaired by intracellular repair mechanisms, impairs the cell's ability to replicate its DNA. Examples of alkylating anticancer agents are cyclophosphamide and chlorambucil.

Some anticancer agents target the intracellular mechanisms involved in replication of the DNA strand itself. Replication of a cell's genetic material requires a means to pull the DNA double helix apart into two strands. This separation is typically accomplished by the enzyme topoisomerase I. Disruption of the function of this enzyme results in DNA strand breaks in cells that are dividing, thereby causing the death of the dividing cell. Because cancer cells grow and reproduce at a much faster rate than normal cells, they are more vulnerable to topoisomerase I inhibition than are normal cells. Thus, agents that inhibit topoisomerase I are known to be potent anticancer agents. The drug camptothecin was shown to be an inhibitor of topoisomerase I and a potent anticancer agent. However, it has been observed that camptothecin may produce toxic side effects. In addition, the effectiveness of camptothecin is hampered by both the instability of the molecule itself, resulting in lactone ring opening, and the reversible nature of the inhibition, allowing impacted cells to recover. Therefore, the search for potent inhibitors of topoisomerase I continues.

SUMMARY OF THE INVENTION

Described herein are substituted indenoisoquinolinium compounds, and more specifically substituted 11H-indeno[1,2-c]isoquinolinium compounds. Also described herein are processes for preparing substituted indenoisoquinolinium compounds. Also described herein are methods for treating cancer by administering therapeutically effective amounts of substituted indenoisoquinolinium compounds. In one illustrative embodiment, compounds of formula (I) are described and pharmaceutically acceptable salts, hydrates, and solvates thereof, wherein:

A is hydrogen, optionally substituted alkyl, optionally substituted alkenyl, optionally substituted alkynyl, optionally substituted arylalkyl, optionally substituted heteroarylalkyl, OR, NROR, and NRNRR, where R is in each instance independently selected from hydrogen, optionally substituted allyl, optionally substituted arylalkyl, optionally substituted acyl, optionally substituted alkoxyacyl, optionally substituted arylalkoxyacyl, and optionally substituted alkyl or dialkylaminoacyl; and B is hydrogen or alkyl; or A and B are taken together to form a double-bonded substituent selected from oxygen, optionally substituted alken-1-yl, NOR, and NNRR, where R is in each instance independently selected from hydrogen, optionally substituted alkyl, optionally substituted arylalkyl, optionally substituted acyl, optionally substituted alkoxyacyl, optionally substituted arylalkoxyacyl, and optionally substituted alkyl or dialkylaminoacyl;

$R^6$ is selected from the group consisting of hydrogen, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, and optionally substituted acyl;

$R^a$ represents 1-4 substituents each of which is independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof; or $R^a$ represents 2-4 substituents where 2 of said substituents are adjacent substituents and are taken together with the attached carbons to form an optionally substituted heterocycle, and where any remaining substituents are each independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof;

$R^d$ represents 1-4 substituents each of which is independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof; or $R^d$ represents 2-4 substituents where 2 of said substituents are adjacent substituents and are taken together with the attached carbons to form an optionally substituted heterocycle, and where any remaining substituents are each independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof;

$X^-$ is a anion, including a pharmaceutically acceptable anion.

In one illustrative embodiment of the compounds of formula I, A and B are both hydrogen. In one illustrative aspect, $R^6$ is also hydrogen. In another illustrative aspect, $R^6$ is an optionally substituted alkyl group. In another illustrative embodiment of the compounds of formula I, A and B are taken together to form a double-bonded oxygen. In one illustrative aspect, $R^6$ is hydrogen. In another illustrative aspect, $R^6$ is an optionally substituted alkyl group.

In another illustrative embodiment, compounds of formula II are described wherein m is an integer from 1-6, and Z is selected from halo, hydroxy, alkoxy, cycloalkoxy, haloalkoxy, halocycloalkoxy, optionally substituted aryloxy, optionally substituted heteroaryloxy, acyloxy, amino, alkyl and dialkylamino, trialkylammonium, hydroxyalkylamino, hydroxyalkylaminoalkylamino, acylamino, hydroxylamino, alkoxylamino, acyloxylamino, cycloalkyl, heteroaryl, halocycloalkyl, alkenyl, alkynyl, acyl, cyano, nitro, azido, thio, alkylsulfonyl, carboxylic acid and derivatives thereof, sulfonic acid and derivatives thereof, and phosphonic acid and derivatives thereof.

In one illustrative embodiment of the compounds of formula II, A and B are both hydrogen. In another illustrative embodiment of the compounds of formula II, A and B are taken together to form a double-bonded oxygen. In one aspect of those embodiments, Z is dialkylamino, including dimethylamino, azido, poly(hydroxyalkyl)amino, hydroxyalkylaminoalkylamino, polyhydroxyalkylaminoalkylamino, hydroxyalkyl(alkylamino), heteroaryl, or a combination thereof.

DETAILED DESCRIPTION

In one embodiment, compounds of formula (I) are described and pharmaceutically acceptable salts, hydrates, and solvates thereof, wherein:

A is hydrogen, optionally substituted alkyl, optionally substituted alkenyl, optionally substituted alkynyl, optionally substituted arylalkyl, optionally substituted heteroarylalkyl, OR, NROR, and NRNRR, where R is in each instance independently selected from hydrogen, optionally substituted alkyl, optionally substituted arylalkyl, optionally substituted acyl, optionally substituted alkoxyacyl, optionally substituted arylalkoxyacyl, and optionally substituted alkyl or dialkylaminoacyl; and B is hydrogen or alkyl; or A and B are taken together to form a double-bonded substituent selected from oxygen, optionally substituted alken-1-yl, NOR, and NNRR, where R is in each instance independently selected from hydrogen, optionally substituted alkyl, optionally substituted arylalkyl, optionally substituted acyl, optionally substituted alkoxyacyl, optionally substituted arylalkoxyacyl, and optionally substituted alkyl or dialkylaminoacyl;

$R^6$ is selected from the group consisting of hydrogen, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, and optionally substituted acyl;

$R^a$ represents 1-4 substituents each of which is independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof; or $R^a$ represents 2-4 substituents where 2 of said substituents are adjacent substituents and are taken together with the attached carbons to form an optionally substituted heterocycle, and where any remaining substituents are each independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof;

$R^d$ represents 1-4 substituents each of which is independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof; or $R^d$ represents 2-4 substituents where 2 of said substituents are adjacent substituents and are taken together with the attached carbons to form an optionally substituted heterocycle, and where any remaining substituents are each independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof;

$X^-$ is a anion, including a pharmaceutically acceptable anion.

As used herein, the term "alkyl" refers to a saturated monovalent chain of carbon atoms, which may be optionally branched. It is understood that in embodiments that include alkyl, illustrative variations of those embodiments include lower alkyl, such as $C_1$-$C_6$, $C_1$-$C_4$ alkyl, methyl, ethyl, propyl, 3-methylpentyl, and the like.

As used herein, the term "cycloalkyl" refers to a monovalent chain of carbon atoms, a portion of which forms a ring. It is understood that in embodiments that include cycloalkyl, illustrative variations of those embodiments include lower cycloalkyl, such as $C_3$-$C_8$, $C_3$-$C_6$ cycloalkyl, cyclopropyl, cyclohexyl, 3-ethylcyclopentyl, and the like.

As used herein, the term "alkenyl" refers to an unsaturated monovalent chain of carbon atoms including at least one double bond, which may be optionally branched. It is understood that in embodiments that include alkenyl, illustrative variations of those embodiments include lower alkenyl, such as $C_2$-$C_6$, $C_2$-$C_4$ alkenyl.

As used herein, the term "cycloalkenyl" refers to an unsaturated monovalent chain of carbon atoms, a portion of which forms a ring. It is understood that in embodiments that include cycloalkenyl, illustrative variations of those embodiments include lower cycloalkenyl, such as $C_3$-$C_8$, $C_3$-$C_6$ cycloalkenyl.

As used herein, the term "alkylene" refers to a saturated bivalent chain of carbon atoms, which may be optionally branched. It is understood that in embodiments that include alkylene, illustrative variations of those embodiments include lower alkylene, such as $C_2$-$C_4$, alkylene, methylene, ethylene, propylene, 3-methylpentylene, and the like.

As used herein, the term "heterocycle" refers to a monovalent chain of carbon and heteroatoms, wherein the heteroatoms are selected from nitrogen, oxygen, and sulfur, a portion of which, including at least one heteroatom, form a ring, such as aziridine, pyrrolidine, oxazolidine, 3-methoxypyrrolidine, 3-methylpiperazine, and the like.

It is to be understood that each of alkyl, cycloalkyl, alkenyl, cycloalkenyl, alkylene, and heterocyclyl may be optionally substituted with independently selected groups such as alkyl, haloalkyl, hydroxyalkyl, aminoalkyl, carboxylic acid and derivatives thereof, including esters, amides, and nitriles, hydroxy, alkoxy, acyloxy, amino, allyl and dialkylamino, acylamino, thio, and the like, and combinations thereof.

As used herein, the term "optionally substituted aryl" refers to an aromatic mono or polycyclic ring of carbon atoms, such as phenyl, naphthyl, and the like, which may be optionally substituted with one or more independently selected substituents, such as halo, hydroxy, amino, alkyl or dialkylamino, alkoxy, alkylsulfonyl, cyano, nitro, and the like.

As used herein, the term "optionally substituted heteroaryl" refers to an aromatic mono or polycyclic ring of carbon atoms and at least one heteroatom selected from nitrogen, oxygen, and sulfur, such as pyridinyl, pyrimidinyl, indolyl, benzoxazolyl, and the like, which may be optionally substituted with one or more independently selected substituents, such as halo, hydroxy, amino, alkyl or dialkylamino, alkoxy, alkylsulfonyl, cyano, nitro, and the like.

As used herein, the term "acyl" refers to hydrogen, alkyl, cycloalkyl, alkenyl, cycloalkenyl, heterocyclyl, optionally substituted aryl, optionally substituted arylalkyl, optionally substituted heteroaryl, and optionally substituted heteroarylalkyl attached as a substituent through a carbonyl (C=O) group, such as formyl, acetyl, pivalolyl, benzoyl, phenacetyl, and the like.

As used herein, the terms "dialkylamino," "dialkylammonium," and "trialkyammonium" refer to amino substituted with alkyl groups, where each alkyl group is independently selected, and illustratively includes dimethylamino, methylethylamino, diisopropylethylammonium, benzyldimethylammonium, benzyldiisopropylammonium, and the like.

As used herein, the terms "protected hydroxy" and "protected amino" refer to hydroxy and amino groups, respectively, that are protected with a protecting group. It is to be understood that such protecting groups are conventional and routinely selected to allow a synthetic or chemical transformation to be performed in a manner that the hydroxy group or amino group does not interfere with or is not changed by the synthetic or chemical transformation performed. Illustrative, but not exclusive, examples of such protecting groups may be found in Greene & Wuts "Protective Groups in Organic Synthesis," 2d Ed., John Wiley & Sons, New York, 1991, the disclosure of which is incorporated herein by reference. Further illustrative of such protecting groups are those particularly suited for protecting phenols and catechols, and analogs and derivatives thereof.

In one illustrative embodiment of the compounds of formula I, A and B are both hydrogen. In another embodiment, A and B are taken together to form a double-bonded oxygen. In another embodiment, A and B are taken together to form a double-bonded substituent selected from optionally substituted alken-1-yl, NOR, and NNRR, where R is as defined in formula I. In another embodiment, $R^6$ is not optionally substituted phenyl, alkyl, or alkyl substituted with hydroxy, alkenyl, alkylamino, hydroxyalkylamino, phenyl, formyl, or carboxylic acid or ester, when A and B are both hydrogen. In another embodiment, $R^6$ is not hydrogen when $R^6$ is 2,3-dimethoxy and $R^d$ is 7,8-dimethoxy. In another embodiment, $R^6$ is not hydrogen when $R^a$ is 2,3-dimethoxy and $R^d$ is 7,8-methylendioxy.

In another illustrative embodiment, compounds of formula II are described (II)

wherein m is an integer from 1-6, and Z is selected from halo, hydroxy, alkoxy, cycloalkoxy, haloalkoxy, halocycloalkoxy, optionally substituted aryloxy, optionally substituted heteroaryloxy, acyloxy, amino, alkyl and dialkylamino, trialkylammonium, hydroxyalkylamino, hydroxyalkylaminoalkylamino, acylamino, hydroxylamino, alkoxylamino, acyloxylamino, cycloalkyl, heteroaryl, halocycloalkyl, alkenyl, alkynyl, acyl, cyano, nitro, azido, thio, alkylsulfonyl, carboxylic acid and derivatives thereof, sulfonic acid and derivatives thereof, and phosphonic acid and derivatives thereof. In one aspect, Z is dialkylamino, including dimethylamino, azido, poly(hydroxyalkyl)amino, hydroxyalkylaminoalkylamino, polyhydroxyalkylaminoalkylamino, hydroxyalkyl(alkylamino), heteroaryl. or a combination thereof. In another aspect, Z is selected from the formulae each of which may be optionally substituted. In another aspect, m is 2, 3, or 4.

In one embodiment of the compounds of formulae I and II, A and B are both hydrogen. In one aspect of the compounds of formula I, $R^6$ is also hydrogen. In another aspect, $R^6$ is alkyl substituted with amino, dialkylamino, trialkylammonium, poly(hydroxyalkyl)amino, hydroxyalkylaminoalkylamino, (polyhydroxy)alkylaminoalkylamino, heteroaryl, azido, hydroxyalkyl(alkylamino), and combinations thereof. In another aspect, $R^6$ is substituted $C_1$-$C_4$ alkyl. In another aspect, $R^6$ is substituted $C_3$ allyl.

In another embodiment of the compounds of formulae I and II, $R^a$ represents one or more substituents selected from optionally substituted alkoxy. In one aspect, $R^a$ represents at least two adjacent substituents taken together to form alkylenedioxy. In another embodiment, $R^a$ represents one or more substituents selected from hydrogen, halo, hydroxy, amino, alkyl and dialkylamino, nitroso, nitro, hydroxylamino, alkoxylamino, and cyano. In another embodiment of the compounds of formulae I and II, $R^d$ represents one or more substituents selected from optionally substituted alkoxy. In one aspect, $R^d$ represents at least two adjacent substituents taken together to form alkylenedioxy. In another embodiment, $R^d$ represents one or more substituents selected from halo, amino, alkyl and dialkylamino, nitroso, nitro, and cyano.

In another embodiment of the compounds of formulae I and II, A and B are taken together to form a double-bonded oxygen. In one aspect, $R^6$ is hydrogen. In another aspect, $R^6$ is alkyl substituted with amino, dialkylamino, trialkylammonium, poly(hydroxyalkyl)amino, hydroxyalkylaminoalkylamino, (polyhydroxy)alkylaminoalkylamino, heteroaryl, azido, hydroxyalkyl(alkylamino), and combinations thereof. In another aspect, $R^6$ is substituted $C_1$-$C_4$ alkyl. In another aspect, $R^6$ is substituted $C_3$ alkyl. In another aspect, $R^a$ represents one or more substituents selected from optionally substituted alkoxy. In another aspect, $R^a$ represents at least two adjacent substituents taken together to form alkylenedioxy. In another aspect, $R^a$ represents one or more substituents selected from hydrogen, halo, hydroxy, amino, alkyl and dialkylamino, nitroso, nitro, hydroxylamino, alkoxylamino, and cyano. In another aspect, $R^d$ represents one or more substituents selected from optionally substituted alkoxy. In another aspect, $R^d$ represents at least two adjacent substituents taken together to form alkylenedioxy. In another aspect, $R^d$ represents one or more substituents selected from halo, amino, allyl and dialkylamino, nitroso, nitro, and cyano.

In another embodiment, the compounds of the following formulae are described:

where A, B, $R^6$, $R^d$, and $X^-$ are as defined in formula I, R is alkyl or substituted alkyl, and n is an integer from 1 to about 3. In one aspect, A and B are both hydrogen. In another aspect, A and B are taken together to form a double-bonded oxygen.

In another embodiment, the compounds of the following formulae are described:

where A, B, $R^6$, $R^a$, and $X^-$ are as defined in formula I, and R is alkyl or substituted alkyl. In one aspect, A and B are both hydrogen. In another aspect, A and B are taken together to form a double-bonded oxygen.

In another embodiment of the compounds of formulae I and II, A and B are both hydrogen, or A and B are taken together to form a double-bonded oxygen. In one aspect, the substituents $R^a$ are either hydrogen, alkoxy, or alkylenedioxy. In another aspect, the substituents $R^d$ are either hydrogen, alkoxy, or alkylenedioxy. In another aspect, the substituents $R^a$ and the substituents $R^d$ are all either hydrogen, alkoxy, or alkylenedioxy. In another aspect, two adjacent substituents $R^a$ form methylenedioxy or ethylenedioxy. In another aspect, two adjacent substituents $R^d$ form methylenedioxy or ethylenedioxy. In another aspect, $R^a$ represents two substituents at C-2 and C-3, or three substituents at C-1, C-2, and C-3, or at C-2, C-3, and C-4. In another aspect, R represents two substituents at C-8 and C-9, or three substituents at C-7, C-8, and C-9. Compounds illustrative of this embodiment include compounds of the formulae 6, 7, 8, and 9, where n is illustratively 3, and $R^6$ is substituted alkyl for compounds 6, 7, & 8.

| Compounds 6, 7, 8, & 9 | $R^a$ | $R^d$ |
|---|---|---|
| aa | 2,3-dimethoxy | 8,9-dimethoxy |
| ab | 2,3-dimethoxy | 8,9-methylenedioxy |
| ac | 2,3-trimethoxy | 7,8,9-trimethoxy |
| ba | 2,3-methylenedioxy | 8,9-dimethoxy |
| bb | 2,3-methylenedioxy | 8,9-methylenedioxy |
| bc | 2,3-methylenedioxy | 7,8,9-trimethoxy |
| ca | 1,2,3-trimethoxy | 8,9-dimethoxy |
| cb | 1,2,3-trimethoxy | 8,9-methylenedioxy |
| cc | 1,2,3-trimethoxy | 7,8,9-trimethoxy |
| da | 1,4-dimethoxy | 8,9-dimethoxy |
| db | 1,4-dimethoxy | 8,9-methylenedioxy |
| dc | 1,4-dimethoxy | 7,8,9-trimethoxy |
| ea | 2,3,4-trimethoxy | 8,9-dimethoxy |
| eb | 2,3,4-trimethoxy | 8,9-methylenedioxy |
| ec | 2,3,4-trimethoxy | 7,8,9-trimethoxy |

In another illustrative embodiment, A is alkyl, optionally substituted with halo, hydroxy, alkoxy, cycloalkoxy, halo alkoxy, halocycloalkoxy, optionally substituted aryloxy, optionally substituted heteroaryloxy, acyloxy, amino, alkyl and dialkylamino, acylamino, cycloalkyl, halocycloalkyl, alkenyl, alkynyl, acyl, cyano, nitro, azido, alkylsulfonyl, carboxylic acid and derivatives thereof, sulfonic acid and derivatives thereof, and phosphonic acid and derivatives thereof. In another illustrative aspect, A and B are taken together to form alken-1-yl, optionally substituted with halo, hydroxy, alkoxy, cycloalkoxy, haloalkoxy, halocycloalkoxy, optionally substituted aryloxy, optionally substituted heteroaryloxy, acyloxy, amino, alkyl and dialkylamino, acylamino, cycloalkyl, halocycloalkyl, alkenyl, alkynyl, acyl, cyano, nitro, azido, alkylsulfonyl, carboxylic acid and derivatives thereof, sulfonic acid and derivatives thereof, and phosphonic acid and derivatives thereof.

The compounds of formulae I and II may be prepared by the synthetic routes shown in Schemes 1 and 2.

complete reduction of the lactam carbonyl, and partial reduction of the indenone carbonyl to the corresponding hydroxyl group. The reduction may be performed using a variety of conventional reducing agents, including but not limited to borane, borane-THF, $AlH_3$, $LiAlH_4$, $NaBH_4$, $NaCNBH_3$, DIBAL, and the like. Additional details of the synthesis shown in Scheme 1 are described in Strumberg et al., "Synthesis of cytotoxic indenoisoquinoline topoisomerase I poisons," J. Med. Chem. 42:446-57 (1999) and Jayaraman et al., "Synthesis of new dihydroindeno[1,2-c]isoquinoline and indenoisoquinolinium chloride topoisomerase I inhibitors having high in vivo anticancer activity in the hollow fiber animal model," J. Med. Chem. 45:242-49 (2002), the disclosures of which are incorporated herein by reference.

(a) solvent; (b) acid; (c) reducing agent.

(a) 1. metal catalyst, acid, 2. acid;
(b) $O_2$.

Referring to Scheme 2 step (a) shows a dehydration and dehydrogenation of amine 4 to quinolinium 5 with a metal catalyst, such as palladium, platinum, and the like, each of which may be adsorbed onto a carrier such as carbon. Step (b) shows an oxidation of the indene carbon (C-11) of quinolinium 5 to the corresponding indenone 6.

The compounds of formula II, may also be prepared by the synthetic routes shown in Schemes 3 and 4.

Referring to Scheme 1, step (a) shows a condensation between an appropriately $R^a$-substituted anhydride and an appropriately $R^d$-substituted imine that may be performed in a variety of solvents, including but not limited to ether, tetrahydrofuran (THF), N,N-dimethylforamide (DMF), dimethylsulfoxide (DMSO), $CHCl_3$, $CH_2Cl_2$, acetonitrile (ACN), EtOAc, and the like. Step (b) shows an intramolecular Friedel-Crafts reaction of carboxylic acid 1 to form tetracycle 2, which may be performed with conventional reagents, including but not limited to protic acids, such as polyphosphoric acid (PPA), sulfuric acid, and the like, Lewis acids, such aluminum chloride, titanium tetrachloride, boron trichloride, and the like, Eaton's reagent, and dehydrating agents, such as $P_2O_5$, and the like. Step (c) shows a reduction of azide 3 to the corresponding amine 4, with concomitant (a) acid; (b) nucleophile; (c) reducing agent (d) nucleophile, reducing agent, and/or oxidizing agent.

Referring to Scheme 2 steps (a) and (c) are performed as described for Scheme 1. Step (b) shows an optional interconversion of groups Z and Z'. Illustratively, Z is a leaving group, such as halo, alkoxy, and the like, which is displaced by a nucleophile Z', such as an azide salt, different halo, and the like. Step (d) shows another optional interconversion of groups Z or Z' and Z". Illustratively, Z or Z' is a leaving group, such as halo, alkoxy, and the like, which is displaced by a nucleophile Z", such as an azide salt, different halo, and the like. Alternatively, Z or Z' is a group, such as azide, that is reduced to a group Z", such as amino or a salt thereof. Alternatively, Z or Z' is a group, such as hydroxyl, that is oxidized to a group Z", such as carboxylic acid and derivatives thereof. It is to be understood that the stereochemistry shown for the compounds of Schemes 1 and 2 may refer both to the optically active material as well as the racemic material having the relative stereochemistry shown. Illustratively, carboxylic acids 2 have the syn relative stereochemistry of the quinolone substituents, giving the cis ring fusion upon ring closure to diones 3. Upon reduction of 3 to hydroxyl-substituted 4, the corresponding anti configuration between the hydroxy and the ring fusion hydrogens is obtained.

(a) 1. metal catalyst, acid, 2. acid;
(b) $O_2$.

Referring to Scheme 4, steps (a) and (b) are performed as described for Scheme 2. In one aspect, Z" is amino or a salt thereof resulting from the reduction of the corresponding azide. Referring to Scheme 5, step (a) is performed in acetic acid as a solvent resulting in both reduction of the hydroxy substituent and concomitant formation of the acetamide (when Z" is amino or a salt thereof).

(a) 1. metal catalyst, acid, 2. acid;
(b) $O_2$;
(c) acid.

Step (b) shows oxidation at C-11 giving the corresponding acetamide 6a, and step (c) shows acid hydrolysis of the acetamide giving the corresponding amine 7a, as its disalt, such as a dihydrochloride salt when HCl is used as the acid. In contrast, when step (a) in Scheme 5 is performed in formic acid as a solvent, the terminal amino group is unchanged rather than giving the corresponding formamide, to form the corresponding diamine dihydrochloride 8a (as illustrated compounds when Z" is amino or a salt thereof); however, the corresponding dealkylation product 9, also as its hydrochloride salt, is also observed.

The compounds of formulae I and II may also be prepared by the synthetic route shown in Schemes 6.

(a) (MeO)$_2$CHCH$_2$NH$_2$;
(b) reducing agent;
(c) acid.

Referring to Scheme 6 Step (a) shows a condensation of an appropriately R$^a$-substituted aldehyde 10 and aminoacetaldehyde dimethylacetal to form imine 11. It is appreciated that the reaction may be facilitated by removing water during the condensation, illustratively by using a Dean-Stark trap, dehydrating agent, such a MgSO$_4$, Na$_2$SO$_4$, and the like, dessicant, absorbent, molecular sieve, and the like. It is further appreciated that other masked forms of aminoacetaldehyde, including other acetals such as diethylacetals, bisacetoxy acetals, and the like, that may subsequently form oxonium ion intermediates may be used in the condensation shown in step (a). Step (b) shows a reduction of imine 11 to amine 12, using any of a variety of conventional reducing agents, such as NaBH$_4$, LiAlH$_4$, and the like. Step (c) shows an condensation-cyclization of amine 12 with an appropriately R$^d$-substituted aldehyde 10', under acidic conditions. Several acids may be used, including but not limited to trifluoromethanesulfonic, perchloric, polyphosphoric, trifluoroacetic, methanesulfonic, hydrochloric/acetic, sulfuric, and hydrochloric acids.

The indenoisoquinolinium compounds described herein may also form hydrates and solvates. Hydrates may be formed spontaneously upon exposure to ambient conditions where the humidity is sufficient to hydrate the compounds. In addition, hydrates may be formed with more specificity by exposing the compounds described herein to particular humidity conditions. Hydrates may also be formed with by dissolving or suspending the compounds in media containing a predetermined amount of water and evaporating, lyophilizing, or otherwise concentrating such solutions in a manner to give a hydrate form of the compounds described herein. Solvates of the indenoisoquinolinium compounds described herein may also be formed by dissolving or suspending the compounds in a solvent that is capable of forming a complex with the compound, and subsequently evaporating or otherwise concentrating such solutions in a manner to give a solvate form of the compounds described herein. Solvents capable of forming solvates may include alcohols, such as ethanol, butanol, and the like. It is appreciated that both hydrates and solvates of the compounds described herein may have a predetermined stoichiometry. Such stoichiometry may be evaluated by conventional analytical techniques, including X-ray diffraction, melting analysis, and the like.

As used herein, the term "pharmaceutically acceptable anion" includes any nontoxic mono-, di-, or trivalent anions. Exemplary of such anions are HO$^-$, Br$^-$, Cl$^-$, SO$_4^{2-}$, PO$_4^{3-}$, acetate, CO$_3^{2-}$, HCO$_3^-$, and the like. In embodiments of the indenoisoquinolinium compounds described herein that include amino groups, such amino groups may form additional salts. In embodiments of the indenoisoquinolinium compounds described herein that include additional carboxylic acid groups, and derivatives thereof, such groups may also form additional salts, or form inner salts.

The compounds described herein show antineoplastic activity using the COMPARE screening methodology, demonstrating that they are antineoplastic agents useful in treating human cancers. The compounds described herein are inhibitors of topoisomerase I (top1), and in particular may be inhibitors of the top1-catalyzed DNA religation reaction. Such inhibition may account for the antiproliferative activity against cancer cells that compounds described herein show in vitro. The compounds described herein may form ternary complexes consisting of the compound, DNA, and the top1 enzyme. Without being bound by theory, it is believed that the compounds described herein may be operating as top1 poisons, which inhibit the top1 enzyme catalyzed DNA cleavage reaction. It is further appreciated that the compounds described herein may have longer in vitro and in vivo activity than conventional treatments if the formation of the ternary complexes are not reversible or rapidly reversible.

Therefore, some of the growth inhibition demonstrated through COMPARE testing may occur through that mechanism of action, inhibition of topoisomerase I. However, it is appreciated that compounds showing surprisingly potent cell growth inhibition, even though their inhibitory effects on topoisomerase I are relatively small in comparison to other agents tested, may cause inhibition of cell growth, at least in part, through another mechanism of action in addition to or instead of inhibition of topoisomerase I.

Also described herein are pharmaceutical compositions and formulations comprising a therapeutically effective amount of one or more indenoisoquinolinium compounds for treating a patient having cancer. It is appreciated that mixtures of certain indenoisoquinolinium compounds may be administered. Such pharmaceutical compositions may also include one or more diluents, carriers, and/or excipients. As used herein, an effective amount of the indenoisoquinolinium compound is defined as the amount of the compound which, upon administration to a patient, inhibits growth of cancer cells, kills malignant cells, reduces the volume or size of the tumors, and/or eliminates the tumor entirely in the treated patient. It is to be understood that treated patients include humans and other mammals.

As used herein, the term "therapeutically effective amount" refers to the amount to be administered to a patient, and may be based on body surface area, patient weight, and/or patient condition. In addition, it is appreciated that there is an interrelationship of dosages determined for humans and those dosages determined for animals, including test animals (illustratively based on milligrams per meter squared of body surface) as described by Freireich, E. J., et al., *Cancer Chemother. Rep.* 1966, 50 (4), 219, the disclosure of which is incorporated herein by reference. Body surface area may be approximately determined from patient height and weight (see, e.g., Scientific Tables, Geigy Pharmaceuticals, Ardley, N.Y., pages 537-538 (1970)). A therapeutically effective amount of the indenoisoquinolinium compounds described herein may be defined as any amount useful for inhibiting the growth of (or killing) a population of malignant cells or cancer cells, such as may be found in a patient in need of relief from such cancer or malignancy. Typically, such effective amounts range from about 5 mg/kg to about 500 mg/kg, from about 5 mg/kg to about 250 mg/kg, and/or from about 5 mg/kg to about 150 mg/kg of indenoisoquinolinium compounds per patient body weight. It is appreciated that effective doses may also vary depending on the route of administration, optional excipient usage, and the possibility of co-usage of the indenoisoquinolinium compounds with other conventional and non-conventional therapeutic treatments, including other anti-tumor agents, radiation therapy, and the like.

The indenoisoquinolinium compounds may be administered in a variety of pharmaceutical formulations, including conventional pharmaceutical formulations. The indenoisoquinolinium compounds, and formulated variants thereof, may also be delivered by a variety of administration routes, including conventional delivery routes. In one embodiment, the indenoisoquinolinium compounds, and formulated variants thereof, are delivered via a parenteral route, including subcutaneously, intraperitoneally, intramuscularly, and intravenously. Examples of parenteral dosage forms and formulations include aqueous solutions of the indenoisoquinolinium compounds in isotonic saline, 5% glucose or other conventional pharmaceutically acceptable liquid carrier. In one aspect, the one or more indenoisoquinolinium compounds are dissolved in a saline solution containing 5% dimethyl sulfoxide and 10% Cremphor EL (Sigma Chemical Company). Additional solubilizing agents such as cyclodextrins, which can form specific, more soluble complexes with the indenoisoquinolinium compounds described herein, or other conventional solubilizing agents can be included as pharmaceutical excipients for delivery of the compounds.

In another embodiment, the indenoisoquinolinium compounds, and formulated variants thereof, are delivered via oral administration, such as in a capsule, a gel seal, a tablet, and the like. Capsules may comprise any conventional pharmaceutically acceptable material including gelatin and/or cellulose derivatives. Tablets may be formulated by conventional procedures, including by compressing mixtures of the indenoisoquinolinium compounds, solid carriers, lubricants, disintegrants, and other conventional ingredients for solid dosage forms, such as starches, sugars, bentonite, and the like. The compounds described herein may also be administered in a form of a hard shell tablet or capsule containing, for example, lactose or mannitol as a binder, and conventional fillers and tableting agents. Solid dosage forms described herein and useful for delivering the indenoisoquinolinium compounds also include sustained release formulations, such as tablets, caplets, pills, capsules, and the like that include an enteric coating that may delay the release of the indenoisoquinolinium compounds until the formulation has passed into the intestinal tract.

The following exemplary embodiments are included herein to further illustrate the invention. These exemplary embodiments are not intended and should not be interpreted to limit the scope of the invention in any way. It is to be understood that numerous variations of these exemplary embodiments are contemplated herein.

COMPOUND EXAMPLES

Melting points were determined in capillary tubes and are uncorrected. Except where noted, $^1$H NMR spectra were obtained using $CDCl_3$ as solvent and the solvent peak as internal standard. Mass spectra were determined by electrospray mass spectrometry. Reactions were generally monitored by thin-layer chromatography using silica gel flexible sheets, visualized with short wavelength UV light.

2,3-Dimethoxy-6-(3-N-acetylamino-1-propyl)-8,9-(methylenedioxy)-11-oxo-indeno[1,2-c]isoquinolinium Chloride (6ab). The aminoalcohol 4ab (0.26 g, 0.65 mmol) was dissolved in acetic acid (50 mL) and added to the suspension of catalyst (Pd/C 5%, 0.2059 g) in acetic acid (24 mL). The reaction mixture was stirred at reflux for 20 h. Then the reaction mixture was cooled and filtered through a thin layer of celite and acetic acid was added (50 mL). HCl (2 M solution in diethyl ether, 6 mL) was added and the mixture was concentrated. The dark solid obtained was washed with ethyl acetate (20 mL) and diethyl ether (20 mL). The solid obtained was dissolved in water (4 mL). Ethanol (1 mL) and a 15% sodium chloride solution (1 mL) were added. The mixture was refrigerated for 6 h and the solid was separated by filtration. The precipitation was repeated using the same conditions. A mixture of salts (an orange solid containing 6ab, 8ab and trace amounts of 5ab, according to the mass spectrum and $^1$H NMR spectrum) was obtained (74.6 mg). Prolonged exposure of the sample (25 mg) to oxygen (in the air) converted most of the compound 5ab present in the mixture into 6ab. Then the sample was dissolved in $CHCl_3$ (150 mL). The filtrate was concentrated to provide the ketone 6ab, a brown solid (16.8 mg), mp 184-187° C. (dec). $^1$H NMR (300 MHz $CD_3OD$) δ 9.31 (s, 1H), 8.10 (s, 1H), 7.54 (s, 1H), 7.42 (s, 1H), 7.18 (s, 1H), 6.24 (s, 2H), 4.13 (s, 3H), 4.06 (s, 3H), 3.43 (t, J=6.0 Hz, 2H), 2.31 (qn, J=6.0 Hz, 2H); high resolution ESIMS m/z (rel intensity) 435.1559 (100, M$^+$) (calculated mass 435.1556); IR (KBr) 3437, 2919, 1709, 1632, 1563, 1499, 1423, 1345, 1322, 1242, 1222, 1210, 1172, 1121, 1034, 991, 924, 864, 765, 688, 585 cm$^{-1}$. Anal. Calcd for $C_{24}H_{23}N_2O_6Cl(H_2O)_3$: C, 54.91; H, 5.57; N, 5.34. Found: C, 55.00; H, 5.59; N, 5.01.

6-(3-Amino-1-propyl)-2,3-dimethoxy-8,9-(methylenedioxy)-1'-oxo-indeno[1,2-c]isoquinolinium Chloride (7ab). The ketone 6ab (7.6 mg, 0.016 mmol) was dissolved in HCl 2 N (25 mL) and the reaction mixture was heated at reflux for 2 h. Then it was concentrated to provide an orange solid (10.4 mg, 100% as evaluated by $^1$H NMR). $^1$H NMR (300 MHz, D$_2$O, 25° C.) δ 9.06 (s, 1H), 7.64 (s, 1H), 7.44 (s, 1H), 7.26 (s, 1H), 6.97 (s, 1H), 6.18 (s, 2H), 4.90 (t, J=7.5 Hz, 2H), 4.02 (s, 3H), 3.99 (s, 3H), 3.28 (t. J=7.2 Hz, 2H), 2.49 (m, 2H); high resolution ESIMS m/z (rel intensity) 393.1452 (100, M$^+$) (calculated mass 393.1450).

(3,4-Dimethoxybenzylidene)-(2,2-dimethoxyethyl)-amine (11a). Aminoacetaldehyde dimethylacetal (11 mL, 10.73 g, 0.102 mol) was dissolved in chloroform (50 mL) and MgSO$_4$ (8.5 g) was added. Then veratraldehyde (10a, 9.22 g, 0.055 mol) was added and the mixture was stirred at room temperature. After 24 h the MgSO$_4$ was filtered out and the filtrate was washed with water (200 mL), brine (200 mL), dried (Na$_2$SO$_4$) and concentrated to provide the imine, a light yellow liquid (13.90 g, 100%). $^1$H NMR (300 MHz, CDCl$_3$) δ8.09 (s, 1H), 7.33 (d, J=1.8 Hz, 1H), 7.07 (dd, J$_1$=1.8 Hz, J$_2$=8.3 Hz 1H), 6.77 (d, J=8.1, 1H), 4.57 (t, J=5.1 Hz, 1H), 3.83 (s, 3H), 3.80 (s, 31H), 3.65 (dd, J$_1$=5.1 Hz, J$_2$=1.2 Hz, 2H), 3.32 (s, 6H).

(3,4-Dimethoxybenzyl)-(2,2-dimethoxyethyl)-amine (12a). Imine 11a (13.90 g, 0.055 mol) was dissolved in ethanol (50 mL) and NaBH$_4$ (4.2 g) was added over 1 h while stirring the reaction mixture at reflux. The reaction was diluted with water (250 mL). The amine was extracted into chloroform (300 mL) washed with water (2×200 mL), brine (200 mL), dried Na$_2$SO$_4$ and concentrated to provide a yellow liquid (12.88 g, 91.7%). $^1$H NMR (300 MHz CDCl$_3$) 6.81 (s, 1H), 6.78 (d, J=8.1 Hz, 1H), 6.74 (d, J=8.1, 1H), 4.41 (t, J=5.4 Hz, 1H), 3.81 (s, 3H), 3.79 (s, 3H), 3.67 (s, 2H), 3.29 (s, 6H), 2.67 (d, J=5.4 Hz, 2H).

2,3,8,9-Tetramethoxy-11H-indeno[1,2-c]isoquinoline Hydrochloride (9aa). Amine 12a (2.93 g, 0.0115 mmol) and veratraldehyde (10a, 4.11 g) were mixed with concentrated HCl and stirred at 100° C. for 3 h. The reaction mixture was then cooled and washed with ether (50 mL×3). Then it was brought to a basic pH with NH$_4$OH. The mixture was extracted with chloroform (50 mL×4), washed with water (100 mL), dried (Na$_2$SO$_4$) and concentrated. The residue was dissolved in chloroform (200 mL). The mixture was filtered and HCl (2 M in ether, 40 mL) was added to the filtrate. The precipitate that formed was recrystallised from methanol (300 mL) to provide a bright yellow solid (0.5938 g, 14%), mp 254-255° C. $^1$H NMR (300 MHz TFA) δ 9.09 (s, 1H), 7.77 (s, 1H), 7.62 (s, 1H), 7.47 (s, 2H), 7.40 (s, 1H), 4.30 (s, 2H), 4.25 (s, 3H), 4.18 (s, 3H), 4.09 (s, 3H), 4.08 (s, 3H); low resolution ESIMS m/z rel intensity) 338 (100, MH$^+$); IR (KBr) 3434, 2838, 1623, 1582, 1504, 1434, 1413, 1376, 1332, 1240, 1219, 1149, 1099, 999, 829, 513 cm$^{-1}$. Anal. Calcd for $C_{20}H_{20}NO_4Cl(H_2O)_{1.85}$: C, 59.00; H, 5.87; N, 3.44. Found: C, 58.98; H, 5.72; N, 3.49.

2,3-Dimethoxy-8,9-methylenedioxy-1H-indeno[1,2-c]isoquinoline Hydrochloride (9ab). Concentrated HCl (20 mL) was added to a mixture of amine 12a (2.17 g, 8.51 mmol) and piperonal (10b, 3.0 g, 0.020 mol). The reaction mixture was stirred at 100° C. for 3 h. The reaction mixture was then cooled and washed with ether (50 mL×3). Then it was brought to a basic pH with NH$_4$OH. The mixture was extracted with chloroform (50 mL×4), washed with water (100 mL), dried (Na$_2$SO$_4$) and concentrated. The residue was dissolved in a mixture of organic solvents (50 mL diethyl ether, 100 mL dichloromethane, 100 mL chloroform). The mixture was filtered and HCl (2 M in ether, 40 mL) was added to the filtrate. The yellow precipitate that formed (0.806 g, 26%) was collected by filtration, mp 238-240° C. $^1$H NMR (300 MHz D$_2$O) δ 8.30 (s, 1H), 6.91 (s, 1H), 6.69 (s, 1H), 6.44 (s, 1H), 6.39 (s, 1H), 5.94 (s, 2H), 3.78 (s, 3H), 3.77 (s, 3H), 3.00 (s, 2H); low resolution ESIMS m/z (rel intensity) 322 (100, M$^+$); IR (KBr) 3429, 3032, 2611, 1623, 1551, 1504, 1489, 1430, 1413, 1379, 1331, 1296, 1273, 1226, 1206, 1172, 1036, 977, 933, 837, 776, 724 cm$^{-1}$. Anal. Calcd for $C_{19}H_{16}NO_4Cl(H_2O)_{0.85}$: C, 61.17; H, 4.78; N, 3.75. Found: C, 61.19; H, 4.77; N, 3.56.

(3,4-Methylenedioxybenzylidene)-(2,2-dimethoxyethyl) amine (11b). Aminoacetaldehyde dimethylacetal (7.10 g, 0.0666 mol) was dissolved in chloroform (50 mL) and MgSO$_4$ (12 g) was added. Then piperonal (10b, 10.10 g, 0.0666 mol) was added and the mixture was stirred at room temperature. After 24 h there still was unreacted piperonal in the reaction mixture and more amine (6.00 g) was added. The reaction mixture was stirred again at room temperature for 24 h and since there still was some piperonal present more amine (6.00 g) was added again. After stirring the reaction mixture for another 24 h at room temperature the imine was isolated. The reaction mixture was diluted with water (300 mL) and the organic layer was washed with water 200 mL×2, brine (200 mL) dried Na$_2$SO$_4$ and concentrated to provide the pure imine as a yellow oil (15.80 g, 100%). $^1$H NMR (300 MHz, CDCl$_3$) δ 8.13 (s, 1H), 7.33 (s, 1H), 7.07 (d, J=8.10 Hz, 1H), 6.78 (d, J=8.10 Hz, 1H), 5.96 (s, 2H), 4.62 (t, J=5.4 Hz, 1H), 3.70 (d, J=4.2, 2H), 3.83 (s, 6H).

(3,4-Methylenedioxybenzyl)-(2,2-dimethoxyethyl)amine (12b). Imine 11b (10.74 g, 0.045 mol) was dissolved in methanol (100 mL) and NaBH$_4$ (2×3 g) was added over 1 h while stirring the reaction mixture at room temperature. The reaction was quenched with methanol and the reaction mixture was concentrated and then diluted with diethyl ether (400 mL). The precipitate formed was removed by filtration. The filtrate was washed with water (2×200 mL), brine (200 mL), dried (Na$_2$SO$_4$) and concentrated to provide a yellow liquid (4.90 g, 46%). $^1$H NMR (300 MHz CDCl$_3$) 6.79-6.69 (m, 3H), 5.86 (s, 2H), 4.41 (t, J=5.4 Hz, 1H), 3.64 (s, 2H), 3.30 (s, 6H), 2.65 (d, J=5.4 Hz, 2H).

8,9-Dimethoxy-2,3-methylenedioxy-11H-indeno [1,2-c]isoquinoline hydrochloride (9ba). Concentrated HCl (20 mL) was added to a mixture of (3,4-methylenedioxybenzyl)-(2,2-dimethoxyethyl)amine (12b, 1.79 g, 7.49 mmol) and veratraldehyde (10a, 3.04 g, 0.018 mol). The reaction mixture was stirred at 100° C. for 3 h. The reaction mixture was then cooled and washed with ether (50 mL×3). Then it was brought to a basic pH with NH$_4$OH. The mixture was extracted with chloroform (50 mL×4), washed with water (100 mL), dried (Na$_2$SO$_4$) and concentrated. The residue was dissolved in an organic solvent (200 mL chloroform). The mixture was filtered and HCl (2 M in ether, 40 mL) was added to the filtrate. The yellow precipitate that formed (0.7649 g, 29%) was collected by filtration. An analytical sample was prepared by recrystallizing 0.3655 g from methanol (50 mL), mp 257-259° C. $^1$H NMR (300 MHz, TFA) δ 8.88 (s, 1H), 7.69 (s, 1H), 7.39 (s, 1H), 7.33 (s, 2H), 6.21 (s, 2H), 4.18 (s, 2H), 4.02 (s, 3H), 4.01 (s, 3H); low resolution ESIMS m/z (rel intensity) 322 (100, MH$^+$); high resolution ESIMS m/z (rel intensity) 322.1084 (100, MH$^+$) (calculated mass 322.1079); IR (KBr) 3435, 3043, 2966, 2841, 2648, 2027, 1623, 1589, 1494, 1470, 1458, 1419, 1379, 1323, 1291, 1275, 1256, 1220, 1198, 1147, 1122, 1092, 1035, 969, 935, 902, 872, 835, 818, 785, 762, 743, 572 cm$^{-1}$. Anal. Calcd for $C_{19}H_{16}NO_4Cl(H_2O)_{0.7}$: C, 61.61; H, 4.74; N, 3.78. Found: C, 61.40; H, 4.98; N, 3.75.

2,3-Methylenedioxy-8,9-methylenedioxy-11H-indeno[1,2-c]isoquinoline Hydrochloride (9bb). Amine 12b (6.22, 0.0224 mol) and piperonal (10b, 10.10 g, 0.06728 mol) were mixed with concentrated hydrochloric acid (50 mL) and the reaction mixture was stirred at 100° C. for 3 h. Then the reaction mixture was cooled, washed with ether (3×30 mL) and the precipitate formed was dissolved in trifluoroacetic acid (50 mL). The acidic solution was stirred again at 100° C. for 2 h. Then it was diluted with diethyl ether (400 mL). The precipitate was dissolved in methanol:chloroform 3:1 and NH$_4$OH was used to bring the mixture to a basic pH. The mixture was extracted with chloroform (800 mL). The organic layer was filtered, dried (Na$_2$SO$_4$) and concentrated. The residue was washed with chloroform (300 mL) to obtain the base (1.501 g, 22%). Part of the sample was purified further by dissolving the sample in trifluoroacetic acid (50 mL) and adding hydrochloric acid (2 M in diethyl ether, 30 mL). The hydrochloride salt was then washed with ether (200 mL) and recrystallized from methanol (75 mL) to obtain a green-yellow solid, mp 237-239° C. $^1$H NMR (300 MHz, TFA) δ 8.74 (s, 1H), 7.51 (s, 1H), 7.35 (s, 1H), 7.31 (s, 1H), 7.16 (s, 1H), 6.20 (s, 2H), 6.05 (s, 2H), 4.12 (s, 3H); low resolution ESIMS m/z (rel intensity) 306 (100, MH$^+$); IR (KBr) 3425, 3029, 2922, 2474, 2346, 2032, 1699, 1608, 1499, 1468, 1419, 1381, 1355, 1324, 1293, 1242, 1208, 1124, 1065, 1036, 984, 934, 840, 788 cm$^{-1}$. Anal. Calcd for $Cl_8H_{12}NO_4Cl(H_2O)_{0.85}$: C, 60.55; H, 3.87; N, 3.92. Found: C, 60.56; H, 3.96; N, 3.93.

7,8,9-Trimethoxy-2,3-methylenedioxy-11H-indeno[1,2-c]isoquinoline Hydrochloride (9bc). Amine 12b (2.28 g, 9.52 mmol) and 3,4,5-trimethoxybenzaldehyde (10c, 3.77 g, 19.2 mmol) were reacted in trifluoracetic acid (25 mL) with stirring at 100° C. for 3 h. The reaction mixture was cooled and hydrochloric acid (2 M in ether, 10 mL) and ether (200 mL) were added. The precipitate was isolated and dissolved in methanol-water-acetone 1:1:1 (250 mL) and NH$_4$OH was used to bring the mixture to a basic pH. The mixture was extracted with chloroform (350 mL). The organic layer was washed with brine (200 mL), dried (Na$_2$SO$_4$) and concentrated. The residue was dissolved in chloroform (60 mL) and hydrochloric acid (2 M in dry ether, 10 mL) was added. The precipitate was collected and washed with hot methanol (10 mL) and ether 20 (mL) to provide a yellow hygroscopic solid (1.65 g, 45%), mp 257-259° C. $^1$H NMR (300 MHz, CD$_3$OD) δ 9.04 (s, 1H), 7.63 (s, 1H), 7.51 (s, 1H), 7.18 (s, 1H), 6.32 (s, 2H), 4.28 (3H), 4.25 (2H), 3.98 (3H), 3.90 (s, 3H); low resolution ESIMS m/z (rel intensity) 352 (MH$^+$, 100). Anal. Calcd for $C_{20}H_{18}NO_5Cl(H_2O)_{1.9}$: C, 56.92; H, 5.21; N, 3.32. Found: C, 56.92; H, 5.02; N, 3.29.

(3,4,5-Trimethoxybenzylidene)-(2,2-dimethoxyethyl) amine (11c). Aminoacetaldehyde dimethylacetal (20.0 mL, 19.5 g, 0.185 mol) was dissolved in chloroform (80 mL) and MgSO$_4$ (15 g) was added. Then 3,4,5-trimethoxybenzaldehyde (10c, 10.03 g, 0.05112 mol) was also added and the mixture was stirred at room temperature for 24 h. The reaction mixture was diluted with chloroform (70 mL), washed with water (4×150 mL), brine (150 mL), dried (Na$_2$SO$_4$), and concentrated to provide the pure imine as a colorless oil (14.47 g, 100%). $^1$H NMR (300 MHz CDCl$_3$) 8.10 (s, 1H), 6.91 (s, 2H), 4.58 (t, J=5.4 Hz, 1H), 3.81 (s, 6H), 3.79 (s, 3H), 3.69 (s, J$_1$=5.4 Hz, J$_2$=1.2 Hz, 2H), 3.33 (s, 6H).

(3,4,5-Trimethoxybenzyl)-(2,2-dimethoxyethyl)amine (12c). Imine (11c, 14.47 g, 0.05112 mol) was dissolved methanol (100 mL) and NaBH$_4$ (2 g×3) was added over 5 h while stirring the reaction mixture at room temperature. After 3 h the TLC indicated there still was starting material and more NaBH$_4$ (2 g) was added. The reaction did not go to completion leaving 25% of the starting material unreacted. The reaction was quenched with methanol (200 mL) and the reaction mixture was concentrated and then diluted with chloroform (300 μL) and filtered to remove the precipitate. The filtrate was washed with water (4×200 mL), brine (200 mL), dried (Na$_2$SO$_4$), and concentrated. The mixture was dissolved in ethanol (100 mL) and NaBH$_4$ (2.5 g) was added. The reaction was stirred at room temperature for 4 h and then it was heated for 12 h at 80° C. The reaction mixture was diluted with methanol (50 mL) and concentrated. It was then dissolved in chloroform (250 mL) and washed with water (2×300 mL), brine (250 mL), dried (Na$_2$SO$_4$), and concentrated to provide a yellow oil (14.57 g, 100%). $^1$H NMR (300 MHz CDCl$_3$) 6.47 (s, 2H), 4.39 (t, J=5.4 Hz, 1H), 3.76 (s, 6H), 3.73 (s, 3H), 3.65 (s, 2H), 3.28 (s, 6H), 2.65 (d, J=5.4 Hz, 2H).

1,2,3,8,9-Pentamethoxy-11H-indeno[1,2-c]isoquinoline Hydrochloride (9ca). Amine 12c (3.56 g, 0.0125 mol) and veratraldehyde (10a, 4.00 g, 0.0241 mol) were mixed with concentrated hydrochloric acid (25 mL) and the reaction mixture was stirred at 100° C. for 3 h. Then the reaction mixture was cooled and washed with ether (3×30 mL). NH$_4$OH was used to bring the mixture to a basic pH. The mixture was extracted with chloroform (200 mL). The organic layer was filtered, dried (Na$_2$SO$_4$), and concentrated. The residue was dissolved in chloroform (75 mL) and dry hydrochloric acid (40 mL of a 2 M solution in diethyl ether) and diethyl ether (35 mL) were added. The precipitate was collected (crop a). More ether (150 mL) was added and the precipitate was collected (crop b). Crop b was re-precipitated from methanol (50 mL) to yield a yellow solid (0.75 g, 15%), mp 218-220° C. (dec). $^1$H NMR (300 MHz, CD$_3$OD) δ 9.24 (s, 1H), 7.63 (s, 1H), 7.57 (s, 1H), 7.34 (s, 1H), 4.36 (s, 2H), 4.16 (s, 3H), 4.12 (s, 3H), 4.08 (s, 3H), 3.95 (s, 3H), 3.94 (s, 3H); low resolution ESIMS m/z (rel intensity) 368 (100, MH$^+$); IR (KBr) 3414, 2947, 2602, 2346, 1620, 1579, 1545, 1504, 1476, 1441, 1420, 1393, 1371, 1330, 1244, 1220, 1202, 1130, 1084, 1055, 1032, 985, 914, 857, 821, 788, 763 cm$^{-1}$. Anal. Calcd for $C_{21}H_{22}NO_5Cl(H_2O)_{1.6}$: C, 58.29; H, 5.87; N, 3.24. Found: C, 58.32; H, 5.77; N, 3.05.

2,3,4-Trimethoxy-7,8-methylenedioxy-11H-indeno[1,2-c]isoquinoline Hydrochloride (9cb). Amine 12c (2.59 g, 9.08 mmol) and piperonal (10b, 3.50 g, 0.023 mol) were reacted in concentrated hydrochloric acid as described previously for compound 9aa. The product was isolated as a yellow solid (0.62 g, 18%). Reprecipitation of the sample (68.7 mg) from methanol (50 μL) afforded analytically pure material as a hygroscopic solid, mp 230-232° C. (dec). $^1$H NMR (300 MHz, CD$_3$OD) δ 9.29 (s, 1H), 7.62 (s, 1H), 7.53 (s, 1H), 7.26 (s, 1H), 6.11 (s, 2H), 4.41 (s, 2H), 4.16 (s, 3H), 4.11 (s, 3H), 4.08 (s, 3H); low resolution ESIMS m/z (rel intensity) 352 (MH$^+$, 100). Anal. Calcd for $C_{20}H_{18}NO_5Cl(H_2O)_{0.45}$: C, 60.73; H, 4.81; N, 3.54. Found: C, 60.74; H, 4.89; N, 3.48.

1,2,3,7,8,9-Hexamethoxy-11H-indeno[1,2-c]isoquinoline Hydrochloride (9 cc). Amine 12c (2.62 g, 9.19 mmol) and 3,4,5-trimethoxybenzaldelhyde (10c, 3.70, 18.9 mmol) were mixed with concentrated hydrochloric acid (25 mL) and the reaction mixture was stirred at 100° C. for 3 h. Then the reaction mixture was cooled and washed with ether (3×30 mL). $NH_4OH$ was used to bring the mixture to a basic pH. The mixture was extracted with chloroform (300 mL). The organic layer was filtered, dried ($Na_2SO_4$), and concentrated. The residue was dissolved in chloroform (50 mL) and dry hydrochloric acid (20 mL) and ether (50 mL) were added. The precipitate was collected as a yellow solid (1.612 g, 40%), mp 197-199° C. (dec). $^1$H NMR (300 MHz, $CD_3OD$) δ 9.20 (s, 1H), 7.69 (s, 1H), 7.22 (s, 1H), 4.51 (s, 2H), 4.29 (s, 3H), 4.17 (s, 3H), 4.12 (s, 3H), 4.08 (s, 3H), 3.99 (s, 3H), 3.90 (s, 3H); low resolution ESIMS m/z (rel intensity) 398 (100, $MH^+$); IR (KBr) 3402, 2947, 2352, 2345, 1620, 1580, 1535, 1479, 1426, 1393, 1329, 1237, 1209, 1136, 1055, 980, 947, 913, 784, 504 $cm^{-1}$. Anal. Calcd for $C_{22}H_{24}NO_6Cl(H_2O)_{1.95}$: C, 56.34; H, 6.00; N, 2.99. Found: C, 56.36; H, 5.94; N, 2.92.

(2,5-Dimethoxybenzylidene)-(2,2-dimethoxyethyl)amine (11d). Aminoacetaldehyde dimethylacetal (20.0 mL, 19.5 g, 0.185 mol) was dissolved in chloroform (100 mL) and $MgSO_4$ (10 g) was added. Then 2,5-dimethoxybenzaldehyde (10d, 7.00 g, 0.042 mol) was also added and the mixture was stirred at room temperature for 24 h. The reaction mixture was diluted with chloroform (100 mL), washed with water (2×200 mL), brine (200 mL), dried ($Na_2SO_4$), and concentrated to provide the pure imine as a yellow oil (10.64 g, 100%). $^1$H NMR (300 MHz $CDCl_3$) 8.66 (s, 1H), 7.47 (d, J=3.0 Hz, 1H), 6.91 (dd, $J_1$=9.0 Hz, $J_2$=3.0 Hz, 1H), 6.81 (d, J=9.0 Hz, 1H), 4.65 (t, J=5.1 Hz, 1H), 3.78 (s, 3H), 3.77 (s, 3H), 3.76 (dd, $J_1$=5.4 Hz, $J_2$=1.2 Hz, 2H), 3.38 (s, 6H).

(2,5-Dimethoxybenzyl)-(2,2-dimethoxyethyl)amine (12d). Amine 11d (10.64 g, 0.042 mol) was dissolved in ethanol (100 mL) and $NaBH_4$ (2.6 g) was added and the reaction mixture was stirred at 80-90° C. After 3 h the TLC indicated the absence of the starting material. The organic layer was washed with water (2×200 mL), brine (200 mL), dried ($Na_2SO_4$) and concentrated to provide a colorless oil (10.71 g, 100%). $^1$H NMR (300 MHz $CDCl_3$) 6.79-6.67 (m, 3H), 4.43 (t, J=5.7 Hz, 1H), 3.72 (s, 3H), 3.71 (s, 3H), 3.68 (d, J=2.7 Hz, 2H), 3.28 (s, 6H), 2.7 (s, 2H).

1,4,7,8-Tetramethoxy-11H-indeno[1,2-c]isoquinoline Hydrochloride (9da). Amine 12d (2.82 g, 11.1 mmol) and veratraldehyde (10a, 4.00 g, 0.030 mol) were reacted in concentrated hydrochloric acid as described previously for compound 9aa. The product was isolated as a yellow-orange hygroscopic solid (1.01 g, 24%), mp 242-244° C. $^1$H NMR (300 MHz, TFA) δ 9.52 (s, 1H), 7.75 (s, 1H), 7.43 (d, J=7.8 Hz, 1H), 7.38 (s, 1H), 7.08 (d, J=8.7 Hz, 1H), 4.56 (s, 2H), 4.10 (s, 3H), 4.09 (s, 3H), 4.04 (s, 6H). Anal. ($C_{20}H_{20}NO_4Cl.1.7H_2O$)C, H, N, Anal. Calcd for $C_{20}H_{20}NO_4Cl(H_2O)_{1.7}$: C, 59.39; H, 5.83; N, 3.46. Found: C, 59.22; H, 5.53; N, 3.72.

1,4-Dimethoxy-8,9-methylenedioxy-11H-indeno[1,2-c]isoquinoline Hydrochloride (9db). Amine 12d (2.22 g, 8.69 mmol) and piperonal (10b, 3.96 g, 0.0264 mol) were mixed with concentrated hydrochloric acid (50 mL) and the reaction mixture was stirred at 100° C. for 3 h. Then the reaction mixture was cooled and washed with ether (3×50 mL). $NH_4OH$ was used to bring the mixture to a basic pH. The mixture was extracted with chloroform (300 mL). The organic layer was filtered, dried ($Na_2SO_4$) and concentrated. The residue was dissolved in chloroform (100 mL) and dry hydrochloric acid (20 mL) was added and the precipitate was collected (1.397 g, crop a). Then more ether (80 mL) was added and the precipitate was collected again and recrystallized from methanol (50 mL) to provide an orange solid (crop b, 0.2111 g product) (total product 1.6081 g, 51.7%), mp 245-247° C. (dec.). $^1$H NMR (300 MHz, $CD_3OD$) δ 9.50 (s, 1H), 7.56 (s, 1H), 7.48 (d, J=8.7 Hz, 1H), 7.28 (s, 1H), 7.17 (d, J=8.7 Hz, 1H), 6.13 (s, 2H), 4.47 (s, 2H), 4.10 (s, 6H); low resolution ESIMS m/z (rel intensity) 322 (100, $MH^+$); IR (IBr) 3414, 3027, 2943, 2906, 2841, 2013, 1917, 1623, 1599, 1586, 1560, 1504, 1478, 1460, 1426, 1388, 1321, 1290, 1244, 1232, 1159, 1121, 1100, 1035, 1009, 968, 937, 902, 843 $cm^{-1}$. Anal. Calcd for $C_{19}H_{16}NO_4Cl(H_2O)_{0.5}$: C, 62.22; H, 4.67; N, 3.82. Found: C, 62.01; H, 4.83; N, 3.54.

(2,3,4-Trimethoxybenzylidene)-(2,2-dimethoxyethyl)amine (11e). 2,3,4-Trimethoxybenzaldehyde (10e, 11.48 g, 0.05851 mol) was dissolved in benzene (200 mL) and aminoacetaldehydedimethylacetal (10.0 mL, 9.75 g, 0.0927 mol) was added. The same procedure was applied as for 11a. The product was isolated as a clear light yellow oil (16.58 g, 100%), bp 153-155° C. (0.45 mm Hg). $^1$H NMR (300 MHz $CDCl_3$) 8.49 (s, 1H), 7.64 (d, J=8.7 Hz, 1H), 6.65 (d, J=8.7 Hz, 1H), 4.61 (t, J=5.4 Hz, 1H), 3.88 (s, 3H), 3.84 (s, 3H), 3.82 (s, 3H), 3.71 (d, J=5.4 Hz, 2H), 3.36 (s, 6H); low resolution ESIMS m/z (rel intensity) 284 ($MH^+$, 100), 252 (45). Anal. Calcd for $C_{14}H_{21}NO_5$: C, 59.35; H, 7.47; N, 4.94. Found: C, 59.67; H, 7.55; N, 4.88.

(2,3,4-trimethoxybenzyl)-(2,2-dimethoxyethyl)amine (12e). Imine 11e (14.28 g, 0.05040 mol) was dissolved in ethanol (100 mL) and reacted with $NaBH_4$ (3.00 g, 0.0793 mol) as described previously for compound 12a. A colorless oil (14.38 g, 100%) was obtained. $^1$H NMR (300 MHz, $CDCl_3$) δ 6.89 (d, J=8.4 Hz, 1H), 6.57 (d, J=8.4 Hz, 1H), 4.45 (t, J=5.4 Hz, 1H), 3.87 (s, 3H), 3.82 (s, 3H), 3.80 (s, 2H), 3.70 (s, 3H), 3.31 (s, 6H), 2.68 (d, J=5.4 Hz, 2H); low resolution ESIMS m/z (rel intensity) 286 ($MH^+$, 100), 181 (69). Anal. Calcd for $C_{14}H_{23}NO_5$: C, 58.93; H, 8.12; N, 4.91. Found: C, 59.16; H, 8.24; N, 4.64.

1,2,3,7,8-Pentamethoxy-11H-indeno[1,2-c]isoquinoline Hydrochloride (9ea). Amine 12e (2.67, 9.36 mmol) and 3,4-dimethoxybenzaldehyde (10a, 3.23 g, 0.195 mol) were reacted in concentrated hydrochloric acid as described previously for compound 9aa. The product was isolated as a yellow hygroscopic solid (135.5 mg, 5%), mp 201-203° C. $^1$H NMR (300 MHz, $CD_3OD$) δ 9.26 (s, 1H), 7.67 (s, 1H), 7.39 (s, 1H), 7.27 (s, 1H), 4.26 (s, 3H), 4.22 (s, 2H), 4.17 (s, 3H), 3.98 (s, 3H), 3.97 (s, 3H), 3.96 (s, 3H); low resolution ESIMS m/z (rel intensity) 368 ($MH^+$, 100). Anal. Calcd for $C_{21}H_{22}NO_5Cl(H_2O)_{1.8}$: C, 57.81; H, 5.91; N, 3.21. Found: C, 57.91; H, 5.84; N, 2.96.

1,2,3-Trimethoxy-7,8-methylenedioxy-11H-indeno[1,2-c]isoquinoline Hydrochloride (9eb). Amine 12e (3.03, 10.7 mmol) and piperonal (10b, 3.96 g, 0.0264 mol) were reacted in concentrated hydrochloric acid as described previously for compound 9aa. The product was isolated as an yellow hygroscopic solid (0.353 g, 8.5%), mp 206-207° C. $^1$H NMR (300

MHz, CD$_3$OD) δ 9.26 (s, 1H), 7.52 (s, 1H), 7.27 (s, 2H), 6.11 (s, 2H), 4.25 (s, 3H), 4.21 (s, 2H), 4.16 (s, 3H); 3.97 (s, 3H); low resolution ESIMS m/z (rel intensity) 352 (MH$^+$, 100). Anal. Calcd for C$_{20}$H$_{18}$NO$_5$Cl(H$_2$O)$_{0.15}$: C, 61.51; H, 4.72; N, 3.59. Found: C, 61.81; H, 4.85; N, 3.29.

1,2,3,7,8,9-Hexamethoxy-11H-indeno[1,2-c]isoquinoline Hydrochloride (9ec). Amine 12e (3.23, 11.4 mmol) and 3,4,5-trimethoxybenzaldehyde (10d, 4.04 g, 0.0206 mol) were reacted in concentrated hydrochloric acid as described previously for compound 9aa. The product was isolated as a hygroscopic yellow solid (0.5203 g, 10.5%), mp 196-198° C. $^1$H NMR (300 MHz, CD$_3$OD) δ 9.12 (s, 1H), 7.27 (s, 1H), 7.20 (s, 1H), 4.30-4.26 (8H, 4.18 (s, 2H), 3.99 (s, 3H), 3.98 (s, 3H), 3.90 (s, 3H); low resolution ESIMS m/z (rel intensity) 398 (MH$^+$, 100). Anal. Calcd for C$_{22}$H$_{24}$NO$_6$Cl(H$_2$O)$_{1-4}$: C, 57.56; H, 5.88; N, 3.05. Found: C, 57.50; H, 5.98; N, 3.16.

METHOD EXAMPLES

COMPARE screening. The compounds described herein were examined for antiproliferative activity against the human cancer cell lines in the National Cancer Institute screen (COMPARE screening), in which the activity of each compound was evaluated with approximately 55 different cancer cell lines of diverse tumor origins. The GI50 values (i.e., the concentration causing 500% growth inhibition) obtained with selected cell lines, along with the mean graph midpoint (MGM) values, are summarized in Tables 1-3. The MGM is based on a calculation of the average GI50 for all of the cell lines tested (approximately 55) in which GI50 values below and above the test range ($10^{-8}$ to $10^{-4}$ molar) are taken as the minimum ($10^{-8}$ molar) and maximum ($10^{-4}$ molar) drug concentrations used in the screening test. Therefore, the MGM value represents an overall assessment of toxicity of the compound across numerous cell lines. The results of topoisomerase I DNA cleavage experiments are expressed semiquantitatively and provide a means of comparison with the biological activity of other compounds, including NSC 314622 (A) (++) and camptothecin (B) (++++).

TABLE 1

Cytotoxicities$^a$ and Topoisomerase I Inhibitory Activities of Compounds A, B, and 9.

| Tissue | Cell Line | A | B | 9ab | 9aa | 9ba | 9bb | 9bc |
|---|---|---|---|---|---|---|---|---|
| lung | HOP-62 | 1.3 | 0.01 | 0.0721 | NT$^d$ | NT$^d$ | 0.227 | 21.7 |
| colon | HCT-116 | 35 | 0.03 | >100 | >50 | 11.1 | 0.283 | 18.8 |
| CNS | SF-539 | 41 | 0.01 | <0.01 | >50 | 23.4 | 0.598 | NT$^d$ |
| melanoma | UACC-62 | 4.2 | 0.01 | <0.01 | >50 | >100 | 0.19 | 19.3 |
| ovarian | OVCAR-3 | 73 | 0.22 | NT$^d$ | >50 | 61.2 | 0.0232 | 15.5 |
| renal | SN12C | 68 | 0.02 | >100 | >50 | >100 | 0.0414 | 13.4 |
| prostate | DU-145 | 37 | 0.01 | 0.0281 | >50 | 25.3 | NT$^d$ | 23.2 |
| breast | MDA-MB-435 | 96 | 0.04 | <0.01 | >50 | 63.4 | <0.01 | 13.2 |
| MGM$^b$ | | 20 | 0.0405 | 0.0505 | 44.7 | 33.9 | 0.272 | 20.9 |
| Top 1 | Cleavage$^c$ | ++ | ++++ | +++ | ++ | +++ | ++ | 0 |

$^a$The cytotoxicity GI50 values are the concentrations (μM) corresponding to 50% growth inhibition.
$^b$MGM = Mean graph midpoint for growth inhibition of all human cancer cell lines successfully tested.
$^c$The compounds were tested at concentrations ranging up to 10 μM; the activity of the compounds to produce top1-mediated DNA cleavage was expressed semi-quantitatively as follows: 0, no activity; +, weak activity; ++, similar activity as compound A; +++ and ++++, greater activity than compound A; ++++, similar activity as 1 μM camptothecin (B).
$^d$NT = not tested.

TABLE 2

Cytotoxicities$^a$ and Topoisomerase I Inhibitory Activities of Compounds 9.

| Tissue | Cell Line | 9ca | 9cb | 9cc | 9da | 9db | 9ea | 9eb | 9ec |
|---|---|---|---|---|---|---|---|---|---|
| lung | HOP-62 | 34.8 | 0.234 | 35.4 | 21.4 | <0.01 | 16 | NT$^d$ | 28.5 |
| colon | HCT-116 | 31.8 | 0.0694 | 33.5 | 17.8 | 0.249 | 8.81 | 22.1 | 27.8 |
| CNS | SF-539 | 14 | 0.869 | NT$^d$ | 14 | NT$^d$ | NT$^d$ | NT$^d$ | NT$^d$ |
| melanoma | UACC-62 | 7.42 | 0.439 | 17.4 | 18 | >100 | 3.84 | 22.4 | 21.1 |
| ovarian | OVCAR-3 | 15.9 | 0.403 | 19.1 | 15.4 | 26.9 | 0.529 | NT$^d$ | 21.5 |
| renal | SN12C | 14.4 | 0.602 | 17.6 | 14.8 | >100 | NT$^d$ | NT$^d$ | 20.3 |
| prostate | DU-145 | 21.7 | >100 | 26.6 | 28.1 | 48.4 | NT$^d$ | 26.9 | 29.6 |
| breast | MDA-MB-435 | 16.2 | 0.178 | 20.8 | 23.4 | >100 | NT$^d$ | >100 | 23 |
| MGM$^b$ | | 19.1 | 2.01 | 24 | 18.6 | 24.5 | 13.2 | 26.3 | 26.3 |
| Top 1 | Cleavage$^c$ | + | ++ | 0 | 0 | ++ | ++ | ++ | ++ |

$^a$The cytotoxicity GI50 values are the concentrations (μM) corresponding to 50% growth inhibition.
$^b$MGM = Mean graph midpoint for growth inhibition of all human cancer cell lines successfully tested.
$^c$The compounds were tested at concentrations ranging up to 10 μM; the activity of the compounds to produce top1-mediated DNA cleavage was expressed semi-quantitatively as follows: 0, no activity; +, weak activity; ++, similar activity as compound A; +++ and ++++, greater activity than compound A; ++++, similar activity as 1 μM camptothecin (B).
$^d$NT = not tested.

TABLE 3

Cytotoxicities[a] of Compounds 6 and 7.

| Tissue | Cell Line | 6ab | 7ab |
| --- | --- | --- | --- |
| leukemia | SR | 0.0929 | |
| lung | HOP-62 | 1.0 | |
| colon | HCT-116 | 5.08 | |
| CNS | SF-539 | 0.0968 | |
| melanoma | UACC-62 | 3.43 | |
| ovarian | OVCAR-3 | 12.2 | |
| renal | SN12C | 2.76 | |
| prostate | DU-145 | 0.907 | |
| breast | MDA-MB-435 | 0.466 | |
| MGM[b] | | 7.96 | 0.167 |

[a]The cytotoxicity GI50 values are the concentrations (μM) corresponding to 50% growth inhibition.
[b]MGM = Mean graph midpoint for growth inhibition of all human cancer cell lines successfully tested.

Figure 1:
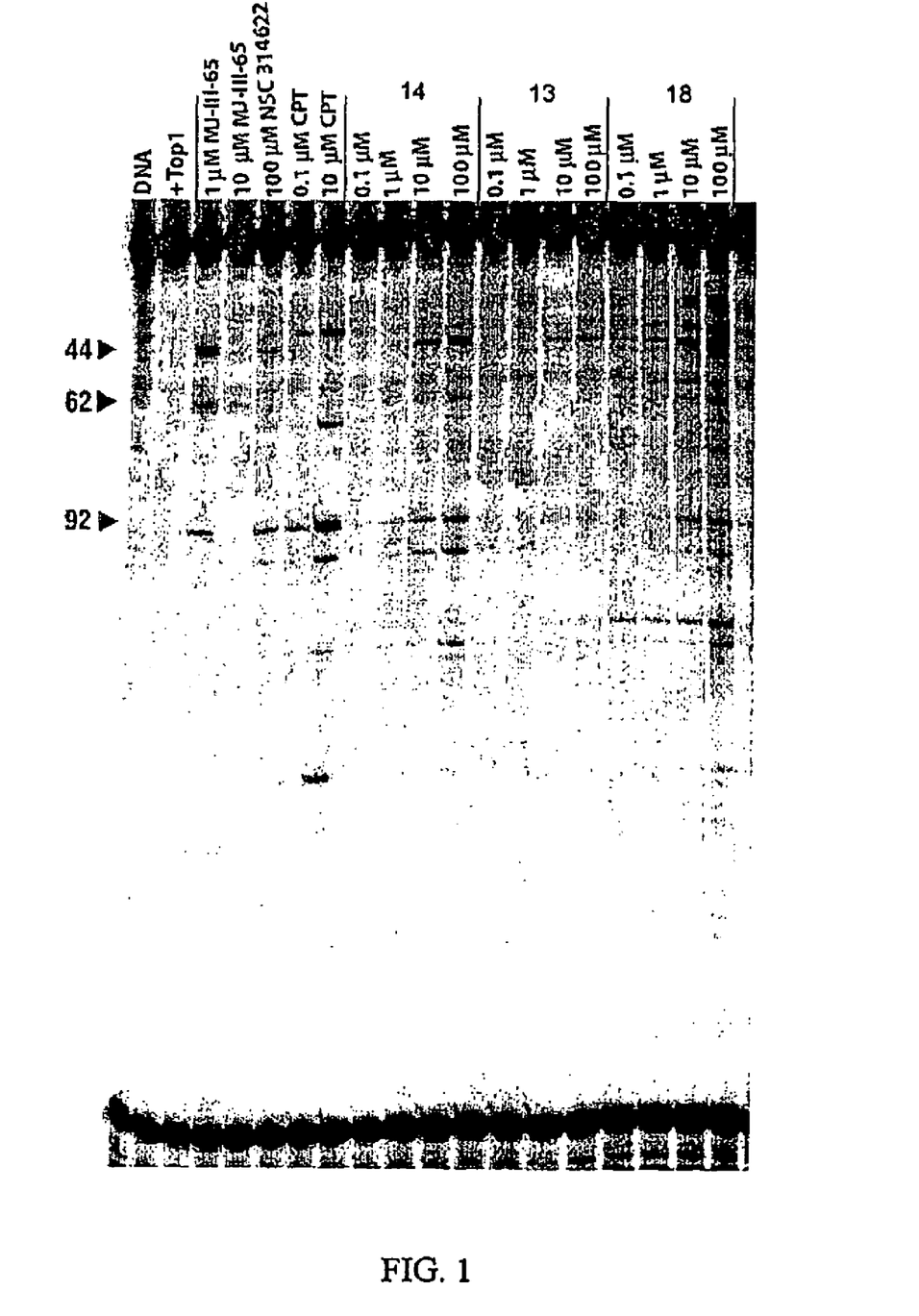
FIG. 1 shows a comparison of the topoisomerase I mediated DNA cleavage products of pBluescript SK(−) phagemid DNA at various drug concentrations as indicated. The assays were carried out at room temperature for 30 min and stopped by adding 0.5% SDS. The resulting DNA fragments were separated using 16% denaturing polyacrylamide gel electrophoresis. Topoisomerase I was present in all reaction mixtures except for the one corresponding to the first lane. Lanes 14 correspond to compound 9ab, lanes 13 to compound 9aa, and lanes 18 to compound 9ba.

Induction of DNA cleavage. The compounds described herein may be examined for induction of DNA cleavage in the 3'-end-labeled PvuII/HindIII fragment of pBluescript SK(−) phagemid DNA in the presence of top1 (see, Kohlhagen et al. "Protein-Linked DNA Strand Breaks Induced by NSC 314622, a Novel Noncamptothecin Topoisomerase I Poison," *Mol. Pharmacol.* 1998, 54, 50-58). The cleavage patterns for compounds 9aa, 9ab, and 9ba are displayed in FIG. 1, along with those of comparative compounds NSC 314622 (A) (see, Kohlhagen et al., "Protein-Linked DNA Strand Breaks Induced by NSC 314622, a Novel Noncamptothecin Topoisomerase I Poison," *Mol. Pharmacol.* 1998, 54, 50-58), camptothecin (B, CPT), and NSC 706744 (C, MJ-III-65) (see, Cushman et al., "Synthesis of New Indeno[1,2-c]isoquinolines: Cytotoxic Non-Camptothecin Topoisomerase I Inhibitors," *J. Med. Chem.* 2000, 43, 3688-3698 and Antony et al., "Differential Induction of Topoisomerase I-DNA Cleavage Complexes by the Indenoisoquinoline MJ-III-65 (NSC 706744) and Camptothecin: Base Sequence Analysis and Activity against Camptothecin-Resistant Topoisomerase I," *Cancer Res.* 2003, 63, 7428-7435). Some, but not all, of the DNA cleavage sites observed with the compounds described herein (namely 9aa, 9ab, and 9ba) were different from each other, and there were also some differences relative to compounds A and C, and to camptothecin. For example, the camptothecin band at site 37 was not seen with A and C or with compounds 9aa, 9ab, and 9ba, as shown in FIG. 1. Further, the band at site 44 was observed with A and C and compounds 9aa, 9ab, and 9ba, but not with camptothecin. Some differences are also apparent in comparison of A and C with compounds 9aa, 9ab, and 9ba.

Topoisomerase I-Mediated DNA Cleavage Reactions Using 3'-End-labeled 161 BP Plasmid DNA. The 161 bp fragment from pBluescript SK(−) phagemid DNA (Stratagene, La Jolla, Calif.) was cleaved with the restriction endonuclease Pvu II and Hind III (New England Biolabs, Beverly, Mass.) in supplied NE buffer 2 (10 μL reactions) for 1 h at 37° C., separated by electrophoresis in a 1% agarose gel made in 1×TBE buffer. The 161 bp fragment was eluted from the gel slice (centrilutor by Amicon) and concentrated in a centricon 50 centrifugal concentrator (Amicon, Beverly, Mass.). Approximately 200 ng of the fragment was 3'-end-labeled at the Hind III site by fill-in reaction with [alpha-$^{32}$P]-dCTP and 0.5 mM DATP, dGTP, and dTTP, in React 2 buffer (50 mM Tris-HCl, pH 8.0, 100 mM MgCl, 50 mM NaCl) with 0.5 units of DNA polymerase I (Klenow fragment). Labeling reactions were followed by phenol-chloroform extraction and ethanol precipitation. The resulting 161 bp 3'-endlabeled DNA fragment was resuspended in water. Aliquots (approximately 50,000 dpm/reaction) were incubated with topoisomerase I at 30° C. for 15 min in the presence of the indicated drug. Reactions were terminated by adding 0.5% SDS. After ethanol precipitation, the samples were resuspended in loading buffer (80% formamide, 10 mM sodium hydroxide, 1 mM sodium EDTA, 0.1% xylene cyanol, and 0.1% bromophenol blue, pH 8.0), and separated in a denaturing gel (16% polyacrylamide, 7 M urea) run at 51° C. The gel was dried and visualized by using a Phosphoimager and ImageQuant software (Molecular Dynamics, Sunnyvale, Calif.).

Topoisomerase II-Mediated DNA Cleavage Assays Using 5'-End-labeled Human C-myc DNA. A 403-base pair DNA fragment of the human c-myc gene from the junction between the first intron and the first exon was prepared by PCR between positions 2671 and 3073 using the a sense primer oligonucleotide and an antisense primer oligonucleotide, as described by Cushman et al., in U.S. Pat. No. 6,509,344. Single-end labeling of these DNA fragments was obtained by 5'-end labeling of the adequate primer oligonucleotide. Approximately 0.1 μg of the human c-myc DNA that had been restricted by XhoI and XbaI was used as template for PCR. The 5'-end-labeled DNA fragments were equilibrated with or without a drug in 1% dimethyl sulfoxide, 10 mM Tris-HCl, pH 7.5, 50 mM KCl, 5 mM MgCl$_2$, 2 mM dithiothreitol, 0.1 mM Na$_2$EDTA, 1 mM ATP, and 15 μg/mL bovine serum albumin for 5 min before addition of purified human topoisomerase II (40-70 ng) in a 10 μL final reaction volume. The reactions were performed at 37° C. for 30 min and thereafter stopped by adding 1% sodium dodecyl sulfate (SDS) and 0.4 mg/mL proteinase K (final concentrations) followed by an additional incubation at 50° C. for 30 min. Samples were ethanol-precipitated before separation of the topoisomerase II-cleaved fragments on denaturing polyacrylamide gels. The sequencing gels were made of 7% polyacrylamide in 1×TBE buffer (90 mM Tris borate, 2 mM EDTA, pH 8.3). Electrophoresis was performed at 2500 V (60 W) for 2-5 h. The gels were dried and visualized using a Phosphoimager and ImageQuant software.

DNA Cleavage Semiquantitative Analysis. One of the most abundant cleavage products, specifically the sequence labeled 44 in FIG. 1 (see, Antony et al., "Differential Induction of Topoisomerase I-DNA Cleavage Complexes by the Indenoisoquinoline MJ-III-65 (NSC 706744) and Camptothecin: Base Sequence Analysis and Activity against Camptothecin-Resistant Topoisomerase I," *Cancer Res.* 2003, 63, 7428-7435) was chosen for semiquantitation using ImageQuant TL v2003.3. The rubberband baseline correction was applied with band detection sensitivity set at 90. In the case of each of the compounds described herein. the absolute density value for the band corresponding to the above product was compared to the value for the NSC 314622 (A). The ratio of the band density observed for the compounds described herein to the NSC 314622 band was multiplied by 100 to obtain percentages. Assignments were performed as follows: 0-25%, 0; 25-75%, +; 75-175%, ++; 175-325%, +++; camptothecin ++++.

SV40 DNA Unwinding Assay. Reaction mixtures (10 μL final volume) contained 0.3 μg supercoiled SV40 DNA in reaction buffer (10 mM Tris-HCl, pH 7.5, 50 mM KCl, 5 mM MgCl$_2$, 0.1 mM EDTA, 15 μg/mL bovine serum albumin) and 10 units of purified calf thymus topoisomerase I. Reactions were performed at 37° C. for 30 min and terminated by the addition of 0.5% SDS, and then 1.1 μL of 10× loading buffer (20% Ficol 400, 0.1 M Na$_2$EDTA pH 8, 1.0% SDS, 0.25% Bromophenol Blue) was then added and reaction mixtures were loaded onto a 1% agarose gel made in 1×TBE buffer.

After electrophoresis, DNA bands were stained in 10 μg/mL of ethidium bromide and visualized by transillumination with UV light (300 nm).

The invention claimed is:
1. A compound of the formula and pharmaceutically acceptable salts thereof, wherein:
A is selected from the group consisting of hydrogen, optionally substituted alkyl, optionally substituted alkenyl, optionally substituted alkynyl, optionally substituted arylalkyl, optionally substituted heteroarylalkyl, OR, NROR, and NRNRR, where R is in each instance independently selected from the group consisting of hydrogen, optionally substituted alkyl, optionally substituted arylalkyl, optionally substituted acyl, optionally substituted alkoxyacyl, optionally substituted arylalkoxyacyl, and optionally substituted alkyl or dialkylaminoacyl; and B is hydrogen or alkyl; providing that A and B are not both hydrogen; or A and B are taken together to form a double-bonded substituent selected from the group consisting of oxygen, optionally substituted alken-1-yl, NOR, and NNRR, where R is in each instance independently selected from the group consisting of hydrogen, optionally substituted alkyl, optionally substituted arylalkyl, optionally substituted acyl, optionally substituted alkoxyacyl, optionally substituted arylalkoxyacyl, and optionally substituted alkyl and dialkylaminoacyl;

$R^6$ is selected from the group consisting of hydrogen, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, and optionally substituted acyl; providing that when either A or B is alkyl, $R^6$ is not alkyl;

$R^a$ represents 1-4 substituents each of which is independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof; or $R^a$ represents 2-4 substituents where 2 of said substituents are adjacent substituents and are taken together with the attached carbons to form an optionally substituted heterocycle, and where any remaining substituents are each independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof;

$R^d$ represents 1-4 substituents each of which is independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof; or $R^d$ represents 2-4 substituents where 2 of said substituents are adjacent substituents and are taken together with the attached carbons to form an optionally substituted heterocycle, and where any remaining substituents are each independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof; and $X^-$ is an anion, including a pharmaceutically acceptable anion.

2. The compound of claim 1 wherein A and B are taken together to form a double-bonded oxygen.
3. The compound of claim 2 wherein $R^6$ is optionally substituted alkyl.
4. The compound of claim 2 wherein $R^6$ is alkyl substituted with optionally substituted aryl, carboxylate and derivatives thereof, halo, hydroxy, alkoxyl, acyloxy, amino, alkylamino, dialkylamino, trialkylammonium, azido, or a combination thereof.
5. The compound of claim 1 wherein one of A or B is hydrogen.
6. The compound of claim 1 wherein $R^a$ is 2,3-dimethoxy or 2,3-methylenedioxy.
7. The compound of claim 1 wherein $R^a$ is 1,4-dialkoxy.
8. The compound of claim 1 wherein $R^a$ is 1,2,3-trialkoxy.
9. The compound of claim 1 wherein $R^a$ is 2,3,4-trialkoxy.
10. The compound of claim 1 wherein $R^d$ is 8,9-dialkoxy.
11. The compound of claim 1 wherein $R^d$ is 7,8,9-trialkoxy.
12. A pharmaceutical composition for treating cancer, the composition comprising:
(a) the compound of claim 1; and
(b) one or more pharmaceutically acceptable carriers, diluents, and excipients therefor;
where the compound is present in an amount effective for treating a cancer in a patient in need of relief; and wherein the cancer is leukemia, lung, colon, CNS, melanoma, ovarian, renal, prostate, or breast cancer, or a combination thereof.
13. The composition of claim 12 wherein A and B are taken together to form a double-bonded oxygen.
14. The composition of claim 12 wherein one of A or B is hydrogen.
15. A method for treating cancer, the method comprising the step of administering a pharmaceutical composition comprising a therapeutically effective amount of the compound of claim 1 to a patient in need of relief from said cancer; wherein the cancer is leukemia, lung, colon, CNS, melanoma, ovarian, renal, prostate, or breast cancer, or a combination thereof.
16. The method of claim 15 wherein the pharmaceutical composition further comprises one or more pharmaceutically acceptable carriers, diluents, and excipients therefor.
17. A process for preparing the compound of claim 1, the process comprising the step of oxidizing a compound of the formula with an oxidizing agent, to prepare a compound of the formula

18. The process of claim 17 wherein $R^6$ is acylamino, aminoalkyl, or a salt thereof.

19. The process of claim 17 wherein the oxidizing agent is atmospheric oxygen.

20. A compound of the formula and pharmaceutically acceptable salts thereof, wherein:
A is selected from the group consisting of hydrogen, optionally substituted alkyl, optionally substituted alkenyl, optionally substituted alkynyl, optionally substituted arylalkyl, optionally substituted heteroarylalkyl, OR, NROR, and NRNRR, where R is in each instance independently selected from the group consisting of hydrogen, optionally substituted alkyl, optionally substituted arylalkyl, optionally substituted acyl, optionally substituted alkoxyacyl, optionally substituted arylalkoxyacyl, and optionally substituted alkyl or dialkylaminoacyl; and B is hydrogen or alkyl; providing that A and B are not both hydrogen when $R^6$ is optionally substituted phenyl, alkyl, or alkyl substituted with hydroxy, alkenyl, alkylamino, hydroxyalkylamino, phenyl, formyl, a carboxylic acid, or a carboxylic ester; or
A and B are taken together to form a double-bonded substituent selected from the group consisting of oxygen, optionally substituted alken-1-yl, NOR, and NNRR, where R is in each instance independently selected from the group consisting of hydrogen, optionally substituted alkyl, optionally substituted arylalkyl, optionally substituted acyl, optionally substituted alkoxyacyl, optionally substituted arylalkoxyacyl, and optionally substituted alkyl and dialkylaminoacyl;
$R^6$ is selected from the group consisting of hydrogen, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, and optionally substituted acyl; providing that when either A or B is alkyl, $R^6$ is not alkyl;
$R^a$ represents 1-4 substituents each of which is independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof; or $R^a$ represents 2-4 substituents where 2 of said substituents are adjacent substituents and are taken together with the attached carbons to form an optionally substituted heterocycle, and where any remaining substituents are each independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof;
$R^d$ represents 1-4 substituents each of which is independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof; or $R^d$ represents 2-4 substituents where 2 of said substituents are adjacent substituents and are taken together with the attached carbons to form an optionally substituted heterocycle, and where any remaining substituents are each independently selected from the group consisting of hydrogen, optionally substituted alkyl, optionally substituted alkoxy, cyano, nitro, optionally substituted alkylsulfonyl, carboxylic acid and derivatives thereof, and sulfonic acid and derivatives thereof; and
$X^-$ is an anion, including a pharmaceutically acceptable anion.

21. The compound of claim 20 wherein A, B, and $R^6$ are each hydrogen.

22. The compound of claim 20 wherein $R^6$ is selected from the group consisting of optionally substituted heteroaryl and optionally substituted heteroarylalkyl.

23. The compound of claim 20 wherein A and B are taken together to form a double-bonded oxygen.

24. The compound of claim 23 wherein $R^6$ is optionally substituted alkyl.

25. The compound of claim 23 wherein $R^6$ is alkyl substituted with optionally substituted aryl, carboxylate and derivatives thereof, halo, hydroxy, alkoxyl, acyloxy, amino, alkylamino, dialkylamino, trialkylammonium, azido, or a combination thereof.

26. The compound of claim 20 wherein $R^6$ is alkyl substituted with optionally substituted aryl, carboxylate and derivatives thereof, halo, hydroxy, alkoxyl, acyloxy, amino, alkylamino, dialkylamino, trialkylammonium, azido, or a combination thereof.

* * * * *